United States Patent [19]

Freeman et al.

[11] Patent Number: 5,693,095
[45] Date of Patent: Dec. 2, 1997

[54] HIGH REFRACTIVE INDEX OPHTHALMIC LENS MATERIALS

[75] Inventors: Charles Freeman, Burleson; David L. Jinkerson, Fort Worth; Mutlu Karakelle, Fort Worth; Albert R. LeBoeuf, Fort Worth, all of Tex.

[73] Assignee: Alcon Laboratories, Inc., Fort Worth, Tex.

[21] Appl. No.: 739,245

[22] Filed: Oct. 29, 1996

Related U.S. Application Data

[63] Continuation of Ser. No. 486,557, Jun. 7, 1995, abandoned.

[51] Int. Cl.$^6$ ............................... A61F 2/16; G02C 7/04; C08F 26/06
[52] U.S. Cl. ........................ 623/6; 526/259; 351/160 H; 351/160 R
[58] Field of Search ..................... 623/6; 351/160 R, 351/160 H; 526/259, 261, 292.1, 292.4, 292.5, 292.6, 292.7

[56] References Cited

U.S. PATENT DOCUMENTS

| | | | |
|---|---|---|---|
| 3,850,892 | 11/1974 | Shen et al. | 160/80.72 |
| 4,036,814 | 7/1977 | Howes et al. | 260/47 |
| 4,260,954 | 4/1981 | Crooks . | |
| 4,267,295 | 5/1981 | Gallop et al. | 526/264 |
| 4,304,895 | 12/1981 | Loshaek | 526/313 |
| 4,393,184 | 7/1983 | Tarumi et al. | 526/261 |
| 4,405,773 | 9/1983 | Loshaek et al. | 526/317 |
| 4,452,776 | 6/1984 | Refojo | 424/81 |
| 4,518,756 | 5/1985 | Yoshida et al. | 526/313 |
| 4,528,311 | 7/1985 | Beard et al. | 524/91 |
| 4,529,747 | 7/1985 | Kato et al. | 523/108 |
| 4,620,954 | 11/1986 | Singer et al. | 264/14 |
| 4,704,006 | 11/1987 | Sakagami et al. | 350/409 |
| 4,761,438 | 8/1988 | Komiya et al. | 523/106 |
| 4,834,750 | 5/1989 | Gupta | 623/6 |
| 5,019,100 | 5/1991 | Hennink et al. | 623/6 |
| 5,269,813 | 12/1993 | Yoshida et al. | 623/6 |
| 5,290,892 | 3/1994 | Namdaran et al. | 526/259 |
| 5,331,073 | 7/1994 | Weinschenk, III et al. | 526/264 |
| 5,359,021 | 10/1994 | Weinschenk, III et al. | 526/264 |
| 5,416,180 | 5/1995 | Yokoyama et al. | 526/245 |
| 5,507,805 | 4/1996 | Koeniger | 623/6 |

FOREIGN PATENT DOCUMENTS

| | | |
|---|---|---|
| 0 136 807 B1 | 4/1985 | European Pat. Off. . |
| 0 273 710 | 7/1988 | European Pat. Off. . |
| 0 391 452 B1 | 10/1990 | European Pat. Off. . |
| 0 485 197A1 | 5/1992 | European Pat. Off. . |
| 95/11279 | 4/1995 | WIPO . |
| 96/11235 | 4/1996 | WIPO . |

OTHER PUBLICATIONS

Koch, D. *Foldable Intaocular Lenses,* Slack Incorporated, Thorofare, NJ, (1993), Chapter 11, "ORC MemoryLens™ A Thermoplastic IOL," pp. 197–212.
Koch, D. *Foldable Intraocular Lenses,* Slack Incorporated, Thorofare, NJ, (1993), Chapter 8, "Alcon AcrySof™ Acrylic Intraocular Lens," pp. 161–177.
Barrett, "A New Hydrogel Intraocular Lens Design," *J. Cataract Refract. Surg.,* vol. 20, pp. 18–25 (1994).
Abstract of Japanese patent document J6 0202–110A published Mar. 26, 1984.
Abstract of Japanese patent document J63109866 published Oct. 28, 1986.
Abstract of Japanese patent document J59136310A published Jan. 26, 1983.

*Primary Examiner*—Paul B. Prebilic
*Attorney, Agent, or Firm*—Patrick M. Ryan

[57] ABSTRACT

Improved soft, foldable acrylic lens materials which are particularly suited for use as IOLs, but which are also useful as other ophthalmic devices, such as contact lenses, keratoprostheses, and corneal rings or inlays, are disclosed. These materials contain only two principal components: one aryl acrylic hydrophobic monomer and one hydrophilic monomer. The materials of the present invention are copolymers comprising at least about 90% by weight of the two principal monomeric components; provided that the amount of the hydrophilic component is not greater than that of the aryl acrylic hydrophobic component. The remainder of the material comprises up to 10% by weight of one or more additional components, such as cross-linking, UV-light absorbing, and blue-light absorbing components.

The aryl acrylic hydrophobic monomers suitable for use in the materials of the present invention have the formula

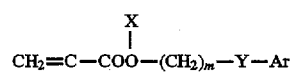

wherein:

X is H or $CH_3$;

m is 0–6;

Y is nothing, O, S, or NR, wherein R is H, $CH_3$, $C_nH_{2n+1}$(n=1–10), iso-$OC_3H_7$, $C_6H_5$, or $CH_2C_6H_5$; and Ar is any aromatic ring which can be unsubstituted or substituted with H, $CH_3$, $C_2H_5$, n-$C_3H_7$, iso-$C_3H_7$, $OCH_3$, $C_6H_{11}$, Cl, Br, $C_6H_5$, or $CH_2C_6H_5$.

29 Claims, No Drawings

HIGH REFRACTIVE INDEX OPHTHALMIC LENS MATERIALS

This application is a continuation of application Ser. No. 08/486,557, filed Jun. 7, 1995 now abandoned.

FIELD OF THE INVENTION

This invention is directed to improved ophthalmic lens materials. In particular, this invention relates to soft, high refractive index ophthalmic lens materials particularly suited for use as intraocular lens ("IOL") materials.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than silicone materials.

U.S. Pat. No. 5,290,892 discloses high refractive index, acrylic materials suitable for use as an IOL material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

SUMMARY OF THE INVENTION

Improved soft, foldable acrylic lens materials which are particularly suited for use as IOLs, but which are also useful as other ophthalmic devices, such as contact lenses, keratoprostheses, and corneal rings or inlays, have now been discovered. These materials contain only two principal components: one aryl acrylic hydrophobic monomer and one hydrophilic monomer. The materials of the present invention are copolymers comprising at least about 90% by weight of the two principal monomeric components; provided that the amount of the hydrophilic component is not greater than that of the aryl acrylic hydrophobic component. The remainder of the material comprises up to 10% by weight of one or more additional components, such as cross-linking, UV-light absorbing, and blue-light absorbing components.

Among other factors, the present invention is based on the finding that acrylic copolymers suitable for use as foldable IOL materials can be synthesized using only one principal acrylic hydrophobic monomer and one principal hydrophilic monomer.

Among other factors, the present invention is also based on the finding that, unlike other acrylic copolymers useful as IOL materials, the copolymers of the present invention are substantially free of glistenings in a physiologic environment

DETAILED DESCRIPTION OF THE INVENTION

The improved acrylic materials of the present invention are copolymers comprising only two principal monomeric components: an aryl acrylic hydrophobic component and a hydrophilic component.

The aryl acrylic hydrophobic monomers suitable for use in the materials of the present invention have the formula

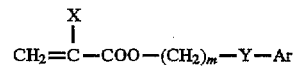

wherein:

X is H or CH$_3$;

m is 0–6;

Y is nothing, O, S, or NR, wherein R is H, CH$_3$, C$_n$H$_{2n+1}$(n=1–10), iso-OC$_3$H$_7$, C$_6$H$_5$, or CH$_2$C$_6$H$_5$; and Ar is any aromatic ring which can be unsubstituted or substituted with H, CH$_3$, C$_2$H$_5$, n-C$_3$H$_7$, iso-C$_3$H$_7$, OCH$_3$, C$_6$H$_{11}$, Cl, Br, C$_6$H$_5$, or CH$_2$C$_6$H$_5$.

Monomers of the above structural formula are described in U.S. Pat. No. 5,290,892, the entire contents of which are hereby incorporated by reference. Preferred aryl acrylic hydrophobic monomers for use in the materials of the present invention are those wherein m is 2–4, Y is nothing or O, and Ar is phenyl. Most preferred are 2-phenylethyl acrylate and 4-phenylbutyl methacrylate.

The homopolymers of the aryl acrylic hydrophobic monomers suitable for use in the present invention contain an equilibrium water content of less than 3%, and preferably less than 2%, by weight as determined gravimetrically in deionized water at ambient conditions.

The hydrophilic monomers suitable for use in the present invention contain at least one reactive, unsaturated functional group. Preferably, the reactive unsaturated functional group is a vinyl, acrylate or methacrylate group.

The homopolymers of the hydrophilic monomers suitable for use in the materials of the present invention have an equilibrium water content of at least 10%, and preferably at least 25%, by weight as determined gravimetrically in deionized water at ambient conditions.

Suitable hydrophilic monomers for use in the present invention include 2-hydroxyethyl acrylate; 2-hydroxyethyl methacrylate; 2-N-ethylacrylate pyrrolidone; 2-hydroxy-3-phenoxypropyl acrylate; 2,3-dihydroxypropyl acrylate; 2,3-dihydroxypropyl methacrylate; 2-N-vinyl pyrrolidone; polyethylene oxide:200 monomethyl ether monomethacrylate; polyethylene oxide:200 monomethacrylate; polyethylene oxide:1000 dimethacrylate.

Preferred hydrophilic monomers for use in the present invention are include 2-hydroxyethyl acrylate; 2-hydroxyethyl methacrylate; and polyethylene oxide:1000 dimethacrylate.

The materials of the present invention are copolymers comprising a total of about 90% by weight of the two principal components described above, provided that the amount of the hydrophilic component is not greater than the aryl acrylic hydrophobic component.

The copolymer materials of the present invention are cross-linked. The copolymerizable cross-linking agent used in the copolymers of this invention may be any terminally ethylenically unsaturated compound having more than one unsaturated group. Combinations of cross-linking monomers are also suitable. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is 1,4-butanediol diacrylate (BDDA). Generally, the amount of the cross-linking component is at least 0.1% (weight).

In addition to an aryl acrylic hydrophobic monomer, a hydrophilic monomer, and one or more cross-linking components, the lens material of the present invention may also contain a total of up to about 10% by weight of additional components which serve other purposes, such as polymerization initiators and reactive UV and/or blue-light absorbers.

Preferred polymerization initiators are peroxy free-radical initiators, such as t-butyl (peroxy-2-ethyl)hexanoate and di-(tert-butylcyclohexyl)peroxydicarbonate (commercially available as Perkadox® 16 from Akzo Chemicals Inc. Chicago, Ill.). Initiators are typically present in an amount of about 5% (weight) or less.

A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1–5% (weight).

Suitable reactive blue-light absorbing compounds, are those described in commonly assigned, copending U.S. Pat. No. 5,470,932, the entire contents of which are hereby incorporated by reference. Blue-light absorbers are typically present in an amount from about 0.01–0.5% (weight).

The particular combination of the two principal monomers described above and the identity and amount of any additional components are determined by the desired properties of the finished ophthalmic lens. Preferably, the ingredients and their proportion are selected so that the improved acrylic lens martials of the present invention possess the following properties, which make the materials of the present invention particularly suitable for use in IOLs which are to be inserted through incisions of 5 mm or less.

The lens material preferably has a refractive index of at least about 1.50 as measured by an Abbe' refractometer at 589 nm (Na light source). Optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably between about −20° to +25° C., and more preferably between about −5° and +16° C. Tg is measured by differential scanning calorimetry at 10° C./min., and is determined at the midpoint of the transition of the heat flux curve.

The lens material will have an elongation of at least 150%, preferably at least 200%, and most preferably between 300 and 600%. This property indicates that the lens generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at standard laboratory conditions of 23°±2° C. and 50±5% relative humidity using an Instron Material Tester model 1122 with a 2000 gram load cell. The grip distance is set at 14 mm and a crosshead speed is set at 20 mm/minute and the sample is pulled to 700% elongation or until failure. The elongation (strain) is reported as a fraction of the displacement at failure to the original grip distance. The modulus is calculated as the instantaneous slope of the stress-strain curve at 100% strain. Stress is calculated at the maximum load for the sample, typically the load when the sample breaks.

The lens materials of the present invention are substantially free of glistenings in a physiologic environment. Glistenings are the result of condensation of water vapor within the lens. Although glistenings have no detrimental effect on the function or performance of IOLs made from acrylic materials, it is nevertheless cosmetically desirable to minimize or eliminate them. An average physiologic temperature is about 37° C. At this temperature in a humid or liquid environment, the materials of the present invention are substantially free of glistenings. It is difficult to quantify what is meant by "substantially free." Nevertheless, in order to provide some frame of reference, "substantially free of glistenings" as used herein generally means that the materials have an average of no more than approximately 1–2 glistenings per $mm^2$ when evaluated in the test described below. Generally, the average number of glistenings per $mm^2$ will be much less than 1.

The presence of glistenings is measured by placement of a lens sample in a test chamber with glass slides on the top and bottom for visualization and filled with deionized water. The chamber is placed in a water bath at 37°±1° C. for 7±1 days and 14±2 days for visualization. The chamber is then placed on a heated microscope stage at. 37°±1° C. and visualized with transmitted light at 40 to 200 times magnification.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens and the haptics are attached to the optic and are like arms which hold the optic in its proper place in the eye. The optic and haptic(s) can be of the same or different material. A multipiece lens is so called became the optic and the haptic(s) are made separately and then the haptics are attached to the optic. In a single piece lens, the optic and the haptics are formed out of one piece of material Depending on the material, the haptics are then cut, or lathed, out of the material to produce the IOL.

In addition to IOLs, the materials of the present invention are also suitable for use as other ophthalmic devices such as contact lenses, keratoprostheses, and corneal inlays or rings.

The invention will be further illustrated by the following examples which are intended to be illustrative, but not limiting.

Examples 1–8, shown below in Table 1, are illustrative of the materials of the present invention. Each of the formulations of Examples 1–8 are prepared as follows, with all of the reactive monomers used being substantially free of inhibitors. After combining the formulation components as listed in Table 1, each formulation is mixed by agitation, purified by passing it through a 0.2 μm polytetrafluoroethylene filter, and then injected into a polypropylene intraocular lens or a 25×12×1 mm slab mold as follows. The bottom portion of the IOL mold contains a cavity which is filled to capacity, and then the top portion of the IOL mold is placed on the bottom portion and locked in place by mating male and female grooves machined into each portion. To make slabs, the cavity in the bottom portion of the slab mold is filled to capacity with the formulation and then the top is placed on strictly as a seal. The molds can either be filled under an inert nitrogen, or standard laboratory atmosphere. To maintain the mold geometry during curing, a means of damping via springs is asserted on the molds. The damped molds are placed in a convection air oven and cured using the curing profiles listed in Table 1. At the end of polymerization period, the molds are opened and the cured intraocular lenses or polymer slabs are removed and extracted in acetone to remove any unreacted materials.

The physical properties of the cured materials shown in Table 1 are then assessed (according to the protocols referred to above) using either the lenses or slabs as appropriate for each testing protocol. All of the formulation examples listed are substantially free of vacuoles.

TABLE 1

| COMPONENT | EXAMPLES | | | | | | | |
|---|---|---|---|---|---|---|---|---|
| | 1 | 2 | 3 | 4 | 5 | 6 | 7 | 8 |
| HEMA | | | | 30 | 35 | | | |
| HEMA | | | | | | 9.8 | 11.8 | 14.7 |
| PEA | | | | 63.5 | 58.5 | 83.5 | 81.5 | 78.6 |
| PEMA | | | 63.1 | | | | | |
| 4-PBMA | 84 | 87.6 | | | | | | |
| PEO | 9.6 | | | | | | | |
| PEGMEMA | | | 29.1 | | | | | |
| BDDA | | | 3.1 | 5 | 5 | 3.1 | 3.1 | 3.1 |
| OMTP | 0.6 | 1 | 1.7 | 0.5 | 0.5 | 1.8 | 1.8 | 1.8 |
| AMA | 2.9 | | | | | | | |
| TEGDA | | 1.5 | | | | | | |
| DDDA | | | | | | | | |
| GMMA | | 7.2 | | | | | | |
| P16 | | | | | | 1.8 | 1.8 | 1.8 |
| tBPO | | | | 1 | 1 | | | |
| BP | 2.9 | 2.7 | 2.9 | | | | | |
| Cure | 2 hrs/80° C. + 3 hrs/100° C. | 2 hrs/80° C. + 3 hrs/100° C. | 2 hrs/80° C. + 3 hrs/100° C. | 1 HR/35 c– 1 HR/50 c– 2 HR/100 c | 1 HR/35 c– 1 HR/50 c– 2 HR/100 c | 25 C. to 70 C. in 10 min, hold 7 hrs, ramp to 100 C. in 30 min, hold 7 | 25 C. to 70 C. in 10 min, hold 7 hrs, ramp to 100 C. 30 min, hold 7 hrs | 25 C. to 70 C. in 10 min, hold 7 hrs, ramp to 100 C. in 30 min, hold 7 hrs |
| Tg | 8.5 | 15.1 | 10.7 | 0 | 0 | 10 | 10 | 11 |
| Stress | 1276 | 1439 | 1320 | 724 | 681 | 982 | 1000 | 1230 |
| % Strain | 461 | 246 | 343 | 392 | 392 | 640 | 610 | 610 |
| Modulus | 362 | 1250 | 623 | 91 | 89 | 97 | 141 | 212 |
| R.I. (dry) | 1.5378 | 1.5409 | 1.5337 | 1.529 | 1.526 | 1.544 | 1.544 | 1.543 |
| R.I. (wet) | 1.5295 | | | | | 1.544 | 1.543 | 1.540 |

HEA = 2-Hydroxyethyl acrylate
HEMA = 2-Hydroxyethyl methacrylate
PEA = 2-Phenylethyl acrylate
PEMA = 2-Phenylethyl methacrylate
4-PBMA 4-Phenylbutyl Methacrylate
AMA = Allyl Methyacrylate
PEO = Polyethylene oxide: 1000 Dimethacrylate
oMTP = o-methallyl Tinuvin P
BP = Benzoyl peroxide
DDDA = 1,12-Dodecanediol Diacrylate
GMMA = 2,3-Dihydroxypropyl Methacrylate
TEGDA = Triethyleneglycol Diacrylate
BDDA = 1,4-Butanediol Diacrylate
PEGMEMA = Polyethylene oxide: 200 monomethyl ether monomethacrylate
tBPO = t-Butyl(peroxy-2-ethyl)hexanoate
P16 = Di-(4-t-butylcyclohexyl)peroxydicarbonate Example 9

Synthesis of the hydrophilic monomer 2-hydroxy-3-phenoxy propylacrylate 1,2 epoxy-3-phenoxypropane (50 g), acrylic acid (48 g, 100% excess), 1,4-benzoquinone (0.082 g), and tetramethylammonium bromide (1.8 g) are placed into a flask and heated under agitation for two hours at 110°–120° C. Following reaction, the volatiles were vacuum distilled off at 0.1–0.2 mm Hg at 100° C. The crude product was then distilled at 170°–175° C. pot temperature. The monomer was dissolved in MeCl and washed with 1% NaOH followed by a water wash. The solution was then dried over anhydrous MgSO$_4$, filtered through #4 paper, and the solvent stripped on rot-o-vap at 50° C.

Example 10

Synthesis of the hydrophilic monomer 2-pyrrolidone-N-2-ethyl acrylate

Step 1—Synthesis of N-(2-hydroxyethyl)-2-pyrrolidone (NHEP): To a 250 ml flask equipped with slanted condenser and condensate receptacle, 107.7 g of 2-aminoethanol and 126.6 g of butyrolactone were added. After several minutes at room temperature there was a vigorous exothermic reaction that peaked at 115° C. Following the exotherm, the flask was placed into a silicone oil bath at 195°–200° C. for 22.5 hours and distillate (mostly water) was collected. The product was then put under high vacuum (0.1 to 0.15 mm Hg) at 115°–150° C. to strip off volatiles. The temperature was then increased to 170°–190° C. and the product (NHEP) distilled.

Step 2—Synthesis of 2-Pyrrolidone-N-2-ethylacrylate (NEAP): Into a 500 ml 63-neck flask equipped with slanted condenser and condensate receptacle was placed 71 g of the NHEP along with 125 g methyl acrylate, 4.1 g phenothiazine, and 2.4 g tetra-butyl titanate. The flask, with contents, was placed into a silicone oil bath at 105°–108° C. and the methyl acrylate-methanol azeotrope collected. The pot was under continuous agitation. After 21 hours of reaction, the methyl acrylate-methanol was stripped off under rot-o-vap at 65° C. and 120 g of fresh methyl acrylate added to the flask contents and the reaction continued for a total reaction time of 48 hours. The methyl acrylate-methanol was again stripped off under rot-o-vap (as above). The crude NEAP was then placed under high vacuum at 65° C. to strip off residual methyl acrylate-methanol. The product was distilled (direct take-over) at 140°–150° C. at 0.1 mm Hg.

Step 3—Final Purification: 50 g of A941-500 basic alumina activity-I[60-325 mesh] placed in a column and flushed with benzene. The NEAP distillate was diluted 50% parts by weight with benzene, and put onto the column—followed by more benzene. A total of 412 grams of eluate was collected and the benzene was stripped off under rotovap at 60° C., followed by high vacuum at 22° C. for 30 minutes. Sufficient deionized water was then added to the NEAP to make a 30 percent solution of the monomer; most of the phenothiazine then precipitates out. The solution was then filtered and then extracted with three 100 ml portions of ether to remove traces of phenothiazine. The water was then evaporated over high velocity air at room temperature followed by high vacuum at room temperature for two hours.

We claim:

1. A copolymer having an elongation of at least 150%, comprising a total of at least 90% by weight of only two principal monomers, wherein one principal monomer is an aryl acrylic hydrophobic monomer of the formula

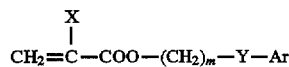

wherein:
X is H or CH$_3$;
m is 0–6;
Y is nothing, O, S, or NR wherein R is H, CH$_3$, C$_n$H$_{2n+1}$(n=1–10) iso-OC$_3$H$_7$, C$_6$H$_5$, or CH$_2$C$_6$H$_5$; and
Ar is any aromatic ring which can be unsubstituted or substituted with H, CH$_3$, C$_2$H$_5$, n-C$_3$H$_7$, iso-C$_3$H$_7$, OCH$_3$, C$_6$H$_{11}$, Cl, Br, C$_6$H$_5$, or CH$_2$C$_6$H$_5$;

the homopolymer of which has an equilibria water content of 3% or less,
and the other principal monomer, present in an amount not greater than the amount of the aryl acrylic hydrophobic monomer, is a hydrophilic monomer having at least one reactive unsaturated functional group, the homopolymer of which has an equilibirum water content of at least 10%,
and wherein the copolymer further comprises a cross-linking monomer having a plurality of polymerizable ethylenically unsaturated groups.

2. The copolymer of claim 1 wherein m is 2–4, Y is nothing or O, and Ar is phenyl.

3. The copolymer of claim 2 wherein the aryl acrylic hydrophobic monomer is selected from the group consisting of 2-phenylethyl acrylate and 4-phenylbutyl methacrylate.

4. The copolymer of claim 1 wherein the unsaturated functional group in the hydrophilic monomer is selected from the group consisting of vinyl, acrylate and methacrylate groups.

5. The copolymer of claim 4 wherein the hydrophilic monomer is selected from the group consisting of 2-hydroxyethyl acrylate, 2-hydroxyethyl methacrylate, 2-N-ethylacrylate pyrrolidone, 2-hydroxy-3-phenoxypropyl acrylate, 2,3-dihydroxypropyl methacrylate, 2-N-vinyl pyrrolidone, polyethylene oxide:200 monomethyl ether monomethacrylate, polyethylene oxide:200 monomethacrylate, and polyethylene oxide:1000 dimethacrylate.

6. The copolymer of claim 5 wherein the hydrophilic monomer is selected from the group consisting of 2-hydroxyethyl acrylate, 2-hydroxyethyl methacrylate, and polyethylene oxide:1000 dimethacrylate.

7. The copolymer of claim 1 further comprising one or more components selected from the group consisting of polymerization initiators, reactive UV absorbers, and reactive blue-light absorbers.

8. The copolymer of claim 1 wherein the copolymer has a refractive index of at least 1.50.

9. The copolymer of claim 1 wherein the copolymer has a Tg from about –20° to +25° C.

10. The copolymer of claim 9 wherein the copolymer has a Tg from about –5° to +16° C.

11. The copolymer of claim 1 wherein the copolymer has an elongation of at least 200%.

12. The copolymer of claim 11 wherein the copolymer has an elongation from 300 to 600%.

13. The copolymer of claim 8 wherein the copolymer has a Tg from about –5° to +16° C. and an elongation from 300 to 600%.

14. An ophthalmic lens comprising a copolymer having an elongation of at least 150%, comprising a total of at least 90% by weight of only two principal monomers, wherein one principal monomer is an aryl acrylic hydrophobic monomer of the formula

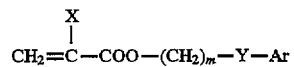

wherein:
X is H or CH$_3$;
m is 0–6;
Y is nothing, O, S, or NR wherein R is H, CH$_3$, C$_n$H$_{2n+1}$(n=1–10) iso-OC$_3$H$_7$, C$_6$H$_5$, or CH$_2$C$_6$H$_5$; and
Ar is any aromatic ring which can be unsubstituted or substituted with H, CH$_3$, C$_2$H$_5$, n-C$_3$H$_7$, iso-C$_3$H$_7$, OCH$_3$, C$_6$H$_{11}$, Cl, Br, C$_6$H$_5$, or CH$_2$C$_6$H$_5$;

the homopolymer of which has an equilibrium water content of 3% or less, and the other principal monomer, present in an amount not greater than the amount of the aryl acrylic hydrophobic monomer, is a hydrophilic monomer having at least one reactive unsaturated functional group, the homopolymer of which has an equilibrium water content of at least 10%, and wherein the copolymer further comprises a cross-linking monomer having a plurality of polymerizable ethylenically unsaturated groups.

15. The ophthalmic lens of claim 14 wherein the lens is an intraocular lens further comprising at least one haptic.

16. The ophthalmic lens of claim 15 wherein m is 2–4, Y is nothing or O, and Ar is phenyl.

17. The ophthalmic lens of claim 16 wherein the aryl acrylic hydrophobic monomer is selected from the group consisting of 2-phenylethyl acrylate and 4-phenylbutyl methacrylate.

18. The ophthalmic lens of claim 16 wherein the unsaturated functional group in the hydrophilic monomer is selected from the group consisting of vinyl, acrylate, and methacrylate groups.

19. The ophthalmic lens of claim 18 wherein the hydrophilic monomer is selected from the group consisting of 2-hydroxyethyl acrylate, 2-hydroxyethyl methacrylate, 2-N-ethylacrylate pyrrolidone, 2-hydroxy-3-phenoxypropyl acrylate, 2,3-dihydroxypropyl methacrylate, 2-N-vinyl pyrrolidone, polyethylene oxide:200 monomethyl ether monomethacrylate, polyethylene oxide:200 monomethacrylate, and polyethylene oxide:1000 dimethacrylate.

20. The ophthalmic lens of claim 19 wherein the hydrophilic monomer is selected from the group consisting of 2-hydroxyethyl acrylate, 2-hydroxyethyl methacrylate, and polyethylene oxide:1000 dimethacrylate.

21. The ophthalmic lens of claim 15 further comprising one or more components selected from the group consisting of polymerization initiators, reactive UV absorbers, and reactive blue-light absorbers.

22. The ophthalmic lens of claim 21 wherein the polymerization initiator is a peroxy free-radical initiator.

23. The ophthalmic lens of claim 22 wherein the reactive UV absorber is 2-(2'-hydroxy-3'-methallyl-5'-methylphenyl) benzotriazole.

24. The ophthalmic lens of claim 15 wherein the intraocular lens has a refractive index of at least 1.50.

25. The ophthalmic lens of claim 15 wherein the intraocular lens has a Tg from about −20° to +25° C.

26. The ophthalmic lens of claim 25 wherein the intraocular lens has a Tg from about −5° to +16° C.

27. The ophthalmic lens of claim 15 wherein the intraocular lens has an elongation of at least 200%.

28. The ophthalmic lens of claim 27 wherein the intraocular lens has an elongation from 300 to 600%.

29. An intraocular lens having an optic consisting essentially of 2-phenylethyl acrylate in an amount of about 80% by weight, 2-hydroxyethyl methacrylate in an amount of about 15% by weight, a cross-linking monomer, a UV-absorber and a polymerization initiator.

* * * * *